United States Patent [19]
Sipinen

[11] Patent Number: 4,808,474
[45] Date of Patent: Feb. 28, 1989

[54] PRESSURE-SENSITIVE ADHESIVE TAPE HAVING IMPROVED TOUGHNESS

[75] Inventor: Alan J. Sipinen, Maplewood, Minn.

[73] Assignee: Minnesota Mining and Manufacturing Company, St. Paul, Minn.

[21] Appl. No.: 27,341

[22] Filed: Mar. 25, 1987

Related U.S. Application Data

[63] Continuation-in-part of Ser. No. 860,557, May 7, 1986, abandoned.

[51] Int. Cl.$^4$ .......................... C09J 7/02; A61F 13/16; B32B 27/08
[52] U.S. Cl. .................................... 428/343; 428/492; 428/500; 428/517; 604/389
[58] Field of Search ............... 428/40, 220, 343, 492, 428/517, 500; 525/240, 229, 211, 51, 193, 202, 88; 524/229; 585/417; 604/389

[56] References Cited

U.S. PATENT DOCUMENTS

| | | | |
|---|---|---|---|
| 3,700,614 | 10/1972 | Schenkerberg | 524/322 |
| 3,941,859 | 3/1976 | Batiuk et al. | 525/211 |
| 3,993,826 | 11/1976 | Butler et al. | 428/220 |
| 4,087,485 | 5/1978 | Huff | 525/193 |
| 4,237,889 | 12/1980 | Gobran | 428/40 X |

Primary Examiner—Thomas J. Herbert
Attorney, Agent, or Firm—Donald M. Sell; Roger R. Tamte

[57] ABSTRACT

Pressure-sensitive adhesive tapes which have improved toughness for use as diaper closure tapes are provided. The tapes have a backing of a substantially untensilized, tough, ductile film that is a blend of crystalline isotactic polypropylene and a compatible flexible polymer, i.e. a polymer having a flexural modulus lower than said crystalline isotactic polypropylene to increase the toughness of the film, and a coating of a pressure-sensitive adhesive on one side of the film.

5 Claims, No Drawings

PRESSURE-SENSITIVE ADHESIVE TAPE HAVING IMPROVED TOUGHNESS

REFERENCE TO RELATED APPLICATION

This application is a continuation-in-part of application Ser. No. 860,557, filed May 7, 1986 now abandoned.

FIELD OF THE INVENTION

This invention relates to a normally tacky, pressure-sensitive adhesive tape having a polyolefin-based backing. The tape is particularly useful for fasteners on disposable diapers.

BACKGROUND OF THE INVENTION

Pressure-sensitive adhesive tapes used as closure tapes on disposable diapers require a special combination of properties. One widely used tape uses paper treated with moisture-resistant polymer as a backing. Paper is a surprisingly expensive material, and its cost is increased by the several treatments to which it is subjected in making the tape suitable for diaper closure use. Further, even treated paper retains a moisture-sensitivity which occasionally weakens it sufficiently to cause it to fail when used in a tape closure for a diaper worn by an active baby. Also, paper is comparatively stiff so that the tape does not flex with the diaper and the edge of a paper tape closure may injure a baby's tender skin.

Cloth-backed tapes can be more attractive, flexible, and tear-resistant than paper but cloth is expensive, special treatments are required to prevent the penetration of adhesive through it, and there is a tendency for it to ravel. Various types of nonwoven tape backings, including the so-called "spun-bonded" polymeric backings are less expensive to make and more ravel-resistant than woven cloth, but their thickness, tear-resistance, etc., are not uniform and their open nature makes application of adhesive coating difficult and expensive.

Film-backing pressure-sensitive adhesive tapes, using backings such a polypropylene, have proven to be generally quite effective for diaper closure tapes but greater latitude in the conditions under which they can be used has also been sought. For example, having tightly closed and adhered one side of a diaper, a person applying the diaper may need to pull strongly on the diaper tape projecting from the other side of the diaper to draw the diaper closed and adhere it in place. This pulling effect, if performed in a rapid or jerky manner, can rupture the tape.

SUMMARY OF THE INVENTION

The present invention provides pressure-sensitive adhesive tapes which have an improved balance of properties, including especially improved toughness needed for use as diaper closures.

One aspect of the invention comprises a pressure-sensitive adhesive tape comprising:

(a) a backing of a substantially untensilized, tough, ductile film, said film comprising a blend of crystalline isotactic polypropylene and a compatible polymer having a flexural modulus lower than that of said crystalline isotactic polypropylene, (hereinafter "flexible polymer"), the film having:

(1) a longitudinal yield tensile strength of at least 160 kg/cm$^2$;

(2) a transverse yield tensile strength of at least 140 kg/cm$^2$;

(3) a longitudinal tear strength of at least about 50 gm/ply;

(4) a tensile impact toughness of greater than about 20 mm/sec; and (b) a coating of a pressure-sensitive adhesive on one side of the film.

The amount of flexible polymer in the blend and the conditions under which the blend is extruded as a film, particularly the chill roll temperature and the length of time the film is in contact therewith, can be varied to achieve the desired toughness and tensile properties. In general, an increase in toughness and decrease in tensile strength is obtained by increasing the amount of flexible polymer, decreasing the chill roll temperature or increasing the chill roll contact time. Surprisingly, high tensile strengths such as listed above can be retained while also achieving high toughness.

This film preferably comprises a blend of a major amount by weight of crystalline, isotactic polypropylene and a minor amount of a compatible flexible polymer, the precise amount of flexible polymer depending on the chosen chill roll temperature and contact time.

Preferred flexible polymers are ethylene-based polymers but other flexible polymers, e.g. elastomers such as styrene-butadiene-styrene block copolymers and styrene-isoprene-styrene block copolymers, have also been found to be useful.

Another aspect of the invention comprises a disposable diaper to which a pressure-sensitive adhesive tape described above is attached as a diaper closure means.

DETAILED DESCRIPTION OF THE INVENTION

A flexible polymer useful in this invention is a polymeric material which has a flexural modulus, as measured by ASTM-D-890, lower than that of the crystalline isotactic polypropylene with which it is blended. The lower flexural modulus will improve the toughness of the blend as compared with that of the crystalline isotactic polypropylene alone. Crystalline isotactic polypropylene generally has a flexural modulus of greater than about 500 megapascal (MPa = 10$^6$N/m$^2$) which means that suitable flexible polymers will generally have a flexural modulus of less than about 500 MPa, preferably less than about 400 MPa. The flexural modulus is also preferably at least about 5 MPa, more preferably at least about 40 MPa.

In general, suitable flexible polymers are also thermoplastic, i.e., they soften or melt to a blendable viscosity. Many of the flexible polymers are elastomers, i.e. when stretched they will retract to assume their original dimensions or nearly so. In particular, preferred elastomers are defined by ASTM Special Technical Bulletin, No 184, wherein a sample is stretched at room temperature to twice its original length, held for a five minute period and released whereupon the sample will return to within 10% of its original length within five minutes.

The flexible polymers must be chemically and/or mechanically compatible with the crystalline isotactic polypropylene to permit effective blending during extrusion and to minimize gross phase separation with aging. Such compatibility can often be assessed, for example, by comparing melt flow characteristics of the flexible polymer with that of the polypropylene, since similar viscosity properties aid in obtaining acceptable blending. The melt indices of both the polypropylene and the flexible polymer can be measured by ASTM Test No. 1238 and the closer the melt indices, the more compatible the blend will be.

The compatibility of the flexible polymer and polypropylene will depend to a certain extent on molecular weight. If the molecular weights are comparable, compatibility will be improved.

Compatibility can also often be determined by using differential scanning calorimetry (DSC) to measure the melting points and glass transition temperatures of the polymer blend. If two glass transition temperatures are detected by DSC due to the constituent polymers in a blend, the blend is said to be incompatible. If a single glass transition temperature, intermediate between those of the component polymers, is detected, the blend is said to be compatible. Mechanically compatible blends represent a deviation from this generality, since they exhibit two glass transition temperatures but have finer morphology and are translucent. Such blends are useful in this invention.

The molecular weights of the polypropylene resin used can have a wide range, preferably in the range of 2 to $4 \times 10^5$. Especially preferred resins have a melt index of from about 8 to 12 grams per 10 minutes. Such polypropylene resins are readily available from commercial sources such as Final Oil and Chemical Company, Deer Park, TX; Exxon Chemical Americas, Houston, TX; Himont USA, Inc., Wilmington, DE; and Shell Chemical Co., Houston, TX.

Ethylene-based flexible polymers are preferred in this invention because of their compatibility with crystalline isotactic polypropylene.

The ethylene-based flexible polymers useful in the present invention may be terpolymers, such as ethylene-propylene-diene (EPDM), copolymers such as ethylene-vinyl acetate (EVA) and ethylene-acrylic acid (EAA), and homopolymers such as low density polyethylene (LDPE) and very low density polyethylene (VLDPE) and combinations thereof.

The ethylene-based terpolymers include elastomeric random or block polymers of ethylene and two other monomers such as propylene and a diene, e.g., 1,4-hexadiene. Preferably, the ethylene content is from about 50 to 70 weight percent, more preferably 55 to 65 weight percent. Preferably, the propylene content is from about 25 to 50 weight percent, more preferably about 35 to 45 weight percent. Preferably, the diene content is from about 0.5 to 4.0 weight percent, more preferably from about 1 to 3 weight percent. In such terpolymers the diene is usually dicyclopentadiene, 1,4-hexadiene, methylene norbornene, ethylidene norbornene, cyclooctadiene and the like.

In a preferred mode of the invention, the EPDM is preblended with a compatible semicrystalline polymer such as high density polyethylene or an ethylene-propylene random or block copolymer having about 0.5 to 4.5 weight percent ethylene for the random copolymer or 0.5 to 10 weight percent ethylene for the block copolymer. The preblend preferably contains 70 to 95 weight percent of the terpolymer and about 5 to 30 weight percent of the high density polyethylene or ethylene-propylene copolymer. The preblend preferably has a melt flow index of about 1 to 4 grams/10 min. The base EPDM rubber preferably has a Mooney viscosity of about 45 at 121° C. and M(60) modulus of about 55 kg/cm. The semicrystalline polymer aids in the dispersion of the EPDM rubber in the polypropylene. The choice of this particular EPDM-based dispersion is by no means limiting and is based on a particular combination of desired properties, ease of dispersion and handling, processability and cost/performance ratio.

Preferred ethylene-based copolymers include ethylene-vinyl acetate and ethylene-acrylic acid copolymers. When the copolymer used is ethylene-vinyl acetate copolymer, the vinyl acetate content is preferably 5 to 50 weight percent, more preferably 10 to 30 weight percent, and the melt index of the copolymer is preferably about 0.2 to 50, more preferably 0.2 to 25. When the copolymer used is ethylene-acrylic acid copolymer, the acrylic acid content is preferably about 5 to 10 weight percent, and the melt index of the copolymer is preferably about 1.5 to 20, more preferably 1.5 to 10.

Other ethylene-based copolymers useful in the present invention include ethylene-propylene copolymers, ethylene-ethyl acrylate copolymers, ethylene-butylene copolymers, ethylene-methyl acrylate copolymers, and ethylene-methyl methacrylate copolymers. Ionomers such as ethylene-zinc acrylate copolymers are also useful.

The very low density polyethylenes useful in the present invention have densities of about 0.9 to 0.91 for example, 0.906 and 0.900, with melt indices of 0.8 and 0.4 respectively. The polyethylenes with densities less than 0.910 are categorized as very low density polyethylenes and have elastomeric character.

Although the preferred ethylene-based copolymers useful in this invention are the terpolymers, copolymers, and very low density polyethylene homopolymers, low density polyethylene may also be used. Low density polyethylenes are catagorized as having densities of 0.925 to 0.910.

Other suitable flexible polymers can be selected from chemical classes such as: styrene-diene block copolymers, thermoplastic polyurethanes and copolyester ethers. Particular properties and sources of flexible polymers of these three classes are disclosed in Kirk-Othmer, *Encyclopedia of Chemical Technology*, Vol. 8, pp. 626–640 (3rd Ed. John Riley & Sons, N.Y., N.Y.) which is incorporated herein by reference.

A desired balance of high tensile strengths and toughness can generally be obtained in the film base of tape of the invention when the polymers are mixed in a range of from about 1 to about 35 weight percent flexible polymer. For especially high tensile strength and good toughness, the flexible polymer is generally present in an amount of 5 to 15 weight percent of the blend. For higher toughness and somewhat lesser tensile strength, the flexible polymer is preferably present in an amount of 15 to 25 weight percent of the blend.

The film base for the tape of the invention is prepared from the above-described blends according to well-known extrusion casting techniques. The flexible polymer and the crystalline isotactic polypropylene components are dry-blended in the desired ratio and fed into an extruder. The film typically can be made by extruding the molten polymer blend at a temperature of about 215° C. to 275° C. through a slot extrusion die and then into a nip between a rubber-covered roll and a water-cooled metal chill roll. In general, the chill roll temperature is 0° C. to 80° C., depending upon the blend composition, roll contact time and desired tensile/modulus properties. Higher chill roll temperatures generally decrease the quench rate and thereby increase the crystallinity of the polypropylene which results in increased tensile strengths, but reduced toughness values and tear strengths. The chill roll may incorporate a shiny chrome finish, matte finish, or engraved pattern, including those disclosed in U.S. Pat. No. 4,237,889. The chill roll contact time will generally be about 0.2 to 1.5 seconds, depending upon roll size, line speed, composition, and desired tensile/modulus properties. An increase in chill roll contact time generally results in reduced tensile strengths and increased toughness values and tear strengths.

The resulting film can be treated by any one or more known techniques, (e.g. corona treatment, flame treatment and ultraviolet irradiation) to enhance surface bonding if desired and wound into a roll. The resulting film is untensilized, i.e., it has not been subjected to longitudinal or transverse stretching after extrusion, although molecular alignment may occur during processing and/or aging.

The incorporation of the flexible polymer in no way precludes incorporation of pigments, fragrances, fillers, and/or dyes. Such materials may be incorporated in amounts up to a total of 10% of the weight of the film without detrimentally affecting the tape. In a preferred embodiment of this invention, pigment is incorporated to impart desired color and opacity to the tape.

The improved physical properties of the films such as tensile strength, tear strength and toughness are obtained in part by controlling the percent crystallinity and spherulite size of the polymer blends which are in turn controlled by the parameters defining the quench rate. The incorporation of flexible polymer results in a decrease in percent crystallinity and spherulite size in the polypropylene matrix. The crystallinity, and thus, tensile strength, modulus and stiffness can be recovered by decreasing the quench rate without sacrificing tensile impact toughness.

The crystallization behavior of isotactic polypropylene is well known. Very rapid rates of crystallization occur as the melt is initially quenched. Secondary crystallization, occurring at a much slower rate, is encountered during the first week after extrusion, after which the crystallization behaviour remains relatively constant. The blending of flexible polymers into polypropylene inhibits the crystallization of polypropylene to a degree dependent upon the nature and amount of added flexible polymer, however, the primary and secondary crystallization processes remain and must be accounted for.

The blended films useful e.g. as tape backings exhibit good tensile strength and tear strength with improved tensile impact toughness over that of known modified or unmodified homopolymer films or blended films. The films are useful as adhesive tape backings requiring high tensile strength and impact toughness, and preferably have the following property characteristics:

(1) a longitudinal yield tensile strength of at least 160 kg/cm$^2$ and more preferably at least about 230 kg/cm$^2$, reaching up to 380 kg/cm$^2$ or more;
(2) a transverse yield tensile strength of at least 140 kg/cm$^2$ and more preferably at least about 210 kg/cm$^2$, reaching up to 360 kg/cm$^2$ or more;
(3) a longitudinal tear strength of at least about 50 gm/ply, and more preferably at least about 150 gm/ply, reaching up to 1000 gm/ply or more;
(4) a tensile impact toughness of greater than about 20 mm/sec, more preferably at least about 40mm/sec and most preferably at least about 120 mm/sec, reaching up to 720 mm/sec or more.

In order to measure these critical property characteristics, the following test procedures were used. Films were aged and then tested a minimum of two weeks after extrusion to ensure equilibrium of properties.

Tensile Strength (ASTM D-882-81):

A 25.4 mm by 150 mm strip of film is mounted in a tensile testing machine e.g. an Instron Tensile Tester with the upper and lower jaws 25.4 mm apart. The jaws are then separated at the rate of 254 mm/minute until the yield point is reached. The machine direction (MD, longitudinal) and cross direction (CD, transverse) of the films were tested after equilibrium was reached (about 2 weeks). Yield tensile strength is reported in kg/cm$^2$.

Tear Strength:

One end of a specimen approximately 75 mm long and exactly 63 mm wide is positioned in a vertical plane with the long dimension extending horizontally, with the ends of the specimen gripped between a pair of fixed clamps horizontally spaced 2.5 mm from a pair of movable clamps which grip the other end of the test specimen. A 20 mm slit is made in the lower edge of the test specimen between the two pairs of clamps. A pendulum, carrying a circumferential graduated scale, is then allowed to fall freely, tearing the pre-cut test specimen along a continuation of the slit. A frictionally mounted pointer on the scale indicates the resistance in grams of the specimen to tearing. This test is commonly referred to as Elmendorf tear strength and values are reported in grams/ply.

Toughness:

Toughness is defined as the ability to withstand a high speed tensile force measured by the ductile/brittle transition. A 25.4 mm by 150 mm strip of film is mounted in a high speed tensile testing machine (MTS Systems) with the upper and lower jaws 25.4 mm apart. Samples are cut with a JDC precision width cutter to reduce the number of edge flaws. A minimum of ten different strain rates are run for each film. Ten samples are run at each strain rate. Samples that show flaws by edge nicks, holes, or tearing rather than clean breaks are not counted among the ten. The number of brittle failures out of 10 good samples are recorded. Brittle failure is defined as samples that break before or at the yield point typically at elongations less than 30%. Ductile samples are defined as those exhibiting a yield point during the test and having elongations typically greater than 100%. The transition from ductile to brittle failure occurs over a range of strain rates. The "brittle onset" is defined as the strain rate at which two out of ten samples show brittle failure and the "brittle endpoint" is defined as the strain rate at which eight out of ten samples show brittle failure. Sample toughness is defined as the brittle onset strain rate or crosshead speed and is reported in mm/sec.

While any increase in toughness over 20 mm/sec is an improvement, toughness values of at least about 40 mm/sec represent a particular improvement. Furthermore, a film having toughness values of at least about 120 mm/sec yields a superior diaper closure tape.

The film backing is converted into tape by applying a coating of normally tacky and pressure-sensitive adhesive to one face, using conventional priming techniques if required. The coating can be a continuous layer or can be discontinuous such as a pattern coating. The adhesive may be transparent or, if desired, colored by incorporating dyes and pigments in a conventional manner. If the uncoated side of the film is exposed at the back of the tape, it may be desirable to apply a release coat such as a silicone polymer or any of several other conventional release coats thereover to facilitate unwinding rolls of the tape. A low release liner which is a silicone coated paper of film may also be used. The tape is normally made on wide sheets of film and then slit to desired widths and lengths and wound convolutely around cores. Diaper closure are formed by cutting appropriately-sized strips (e.g., 2.5 cm×7.5 cm) from the tape.

Where the tape is to be used in making closures for disposable diapers, it is important that the adhesive be capable of bonding firmly to the diaper cover, which is usually polyethylene film. Rubber-resin type pressure-sensitive adhesives are well-suited for this purpose, the "rubber" being either natural rubber or a synthetic copolymer. The type and amount of resin employed will depend on both the rubber and the degree of adhesiveness desired. appropriate adjustments being readily accomplished according to well-known procedures. Acrylate adhesives, e.g., a 94.5:5.5 isooctyl acrylate:acrylic acid copolymer as disclosed in U.S. Pat. No. Re. 24,906, may also be employed. Similarly, if the tape is to be converted into a closure for conventional cloth diapers, it may be desirable to utilize moisture-resistant adhesives of the type disclosed in U.S. Pat. No. 4,074,004.

Disposable diapers normally have a liquid permeable layer designed to be placed next to the skin of the infant, a liquid impermeable layer which forms the outer portion of the diaper in use, and an absorbent layer between the liquid permeable layer and the liquid impermeable layer. The diaper is secured around the infant by a pressure-sensitive adhesive tape closure. A disposable diaper is generally rectangular in shape with closure tapes positioned near one longitudinal end thereof. Two tapes are attached near opposite corners of the outer surface of the liquid impermeable outer layer with a portion of each closure tape extending from the liquid impermeable layer. The portions which extend have a release liner in contact with the pressure-sensitive adhesive on each portion to protect the adhesive prior to fastening. In a preferred embodiment, a release liner is permanently adhered to the inner face of the disposable diaper and a portion of each closure tape is folded over the edges of the disposable diaper to contact the permanently adhered release liners.

This invention is further illustrated by the following examples denoted by numeral which should not be construed to unduly limit the invention. Comparative Examples are denoted by a letter. In the examples, all parts and percentages are by weight unless otherwise indicated.

EXAMPLES 1-14 AND COMPARATIVE EXAMPLES A-C

Film samples were prepared using crystalline isotactic polypropylene homopolymer (PP) ("Dypro" 8771, 95% isotactic polypropylene, density 0.905, available from Fina Oil and Chemical Company, Deer Park, TX); 85% ethulene-propylene-diene terpolymer/15% high density polyethylene (EPDM/PE) ("Nordel" NDR-5501, density 0.87, melt flow index 2.0, available from DuPont Company, Elastomer Chemicals Dept., Wilmington, DE) and polypropylene/titanium dioxide pigment (PP/TiO$_2$) (50% crystalline polypropylene/50% titanium dioxide, density 1.40, available from C.B. Edwards Company, New Hope, MN under the designation 101P) in the amounts shown in Table 1.

The polymers were dry-blended and heated to the molten state. The molten polymer blend was extruded through a slot extrusion die at a temperature shown in Table 1, and then into the nip between a silicone rubber-covered roll having an average roughness (Ra) of 20 and an average maximum profile height (Rpm) of 115, and a water cooled metal chill roll having an Ra of 250 and an Rpm of 220, to effect quenching and provide a matte finish. The roughness properties, Ra and Rpm, were measured with a Surtronic 3, available from Tayler-Hobson, Leichester, England. The temperature of the chill roll and the chill roll contact time are shown in Table 1. The surfaces of the resulting film were primed using conventional corona discharge techniques immediately after extrusion and then aged at room temperature (70° F., 21° C.) for at least two weeks to allow the physical properties to reach equilibrium prior to testing for physical characteristics.

TABLE 1

| Run No. | 1 | 2 | 3 | 4 | 5 | A | 6 | 7 | 8 | 9 | 10 | B | 11 | 12 | 13 | 14 | C |
|---|---|---|---|---|---|---|---|---|---|---|---|---|---|---|---|---|---|
| % PP | 85 | 85 | 75 | 75 | 80 | 95 | 91 | 85 | 91 | 85 | 91 | 95 | 85 | 91 | 85 | 88 | 100 |
| % EPDM | 10 | 10 | 20 | 20 | 20 | 0 | 4 | 10 | 4 | 10 | 4 | 0 | 10 | 4 | 10 | 7 | 0 |
| % PP/TiO$_2$ | 5 | 5 | 5 | 5 | 0 | 5 | 5 | 5 | 5 | 5 | 5 | 5 | 5 | 5 | 5 | 5 | 0 |
| Chill Roll Temp. (°C.) | 7 | 7 | 7 | 7 | 18 | 7 | 9 | 9 | 9 | 9 | 9 | 9 | 9 | 9 | 9 | 9 | 57 |
| Chill Roll Contact Time (sec) | 1.19 | 0.76 | 0.83 | 0.69 | 0.37 | 1.19 | 1.18 | 1.18 | 1.18 | 1.18 | 0.71 | 1.19 | 0.71 | 0.71 | 0.71 | 0.88 | 0.73 |
| Caliper (microns) | 105 | 105 | 105 | 105 | 105 | 105 | 107 | 107 | 123 | 123 | 107 | 105 | 107 | 123 | 123 | 115 | 76 |
| Tensile Strength MD (kg/cm$^2$) | 196 | 216 | 199 | 201 | 223 | 208 | — | — | — | — | — | — | — | — | — | — | — |
| Tensile Strength CD (kg/cm$^2$) | 187 | 192 | 172 | 170 | 198 | 203 | 181 | 164 | 188 | 180 | 223 | 203 | 187 | 261 | 213 | 199 | 276 |
| Tear Strength MD (g/ply) | 194 | 168 | 245 | 160 | 342 | 145 | 176 | 232 | 213 | 256 | 90 | 145 | 146 | 64 | 100 | 178 | 35 |
| Toughness CD (mm/sec) | 212 | 127 | 201 | 170 | 293 | 20 | 318 | 381 | 184 | 296 | 64 | 20 | 191 | 25 | 42 | 169 | 20 |

The data in Table 1 demonstrates that inclusion of the EPDM/PE in the polymer blend increases the toughness of the film produced therefrom, with respect to comparative Examples A-C, while inclusion decreases the tensile and tear strengths to reduced levels that are still acceptable in a diaper closure.

EXAMPLES 15-25

Film samples were prepared as in Examples 1-14, except that the proportions of components were as listed in Table 2. Results are reported in Table 2. Although the cross direction tensile strength for Example 25 is less than 140 kg/cm$^2$, the example is still regarded as within the invention. Also, values of cross direction tensile strength greater than 140 kg/cm² and other properties above the minimum values stated above could be obtained with a composition as recited for Example 25 by using higher chill roll temperatures. Although values for toughness are not reported, measurements on other similar samples indicated that toughness would be well above 120 mm/sec. High values of tear strength were obtained, e.g., most values were higher than 250 gm/ply, which increase the reliability of the tape for diaper closure use.

Chemical Co. under the trade designators Primacor ™ 1410 and 3340, denoted in Table 3 as EAA I and II, respectively, and a styrene/isoprene/ styrene copolymer available from the Shell Chemical Co. were substituted for the EPDM/PE. The compositions, quench conditions, and film properties are set forth in Table 4.

TABLE 2

| Run No. | 15 | 16 | 17 | 18 | 19 | 20 | 21 | 22 | D | 23 | 24 | E | F | G | H | 25 |
|---|---|---|---|---|---|---|---|---|---|---|---|---|---|---|---|---|
| % PP | 75 | 75 | 75 | 75 | 70 | 70 | 70 | 70 | 65 | 65 | 65 | 65 | 60 | 60 | 60 | 60 |
| % EPDM | 20 | 20 | 20 | 20 | 25 | 25 | 25 | 25 | 30 | 30 | 30 | 30 | 35 | 35 | 35 | 35 |
| % PP/TiO$_2$ | 5 | 5 | 5 | 5 | 5 | 5 | 5 | 5 | 5 | 5 | 5 | 5 | 5 | 5 | 5 | 5 |
| Chill Roll Temp. (°C.) | 7 | 24 | 24 | 7 | 7 | 24 | 24 | 7 | 7 | 24 | 24 | 7 | 7 | 24 | 24 | 7 |
| Chill Roll Contact Time (sec.) | 0.8 | 0.8 | 0.8 | 0.8 | 2.0 | 2.0 | 2.0 | 2.0 | 2.0 | 2.0 | 2.0 | 2.0 | 2.0 | 2.0 | 2.0 | 2.0 |
| Caliper (microns) | 105 | 105 | 125 | 125 | 114 | 125 | 135 | 132 | 139 | 134 | 118 | 126 | 120 | 119 | 127 | 139 |
| Tensile Strength MD (kg/cm²) | 171 | 201 | 219 | 193 | 178 | 165 | 175 | 180 | 137 | 175 | 186 | 146 | 120 | 126 | 152 | 163 |
| Tensile Strength CD (kg/cm²) | 155 | 166 | 185 | 180 | 156 | 142 | 151 | 156 | 112 | 146 | 164 | 124 | 95 | 102 | 120 | 134 |
| Tear Strength MD (g/ply) | 249 | 259 | 180 | 235 | 302 | 462 | 592 | 402 | 851 | 526 | 306 | 739 | 954 | 802 | 574 | 642 |

EXAMPLES 26-28

Film samples were prepared as in Examples 1-14, except that the following ethylene-vinyl acetate copolymers (available from DuPont Company, Polymer Products Dept., Wilmington, DE) (hereinafter EVA) were substituted for the EPDM/PE:

| EVA | Percent Vinyl Acetate (wt %) | Melt Index | Trade Designation | Flexural Modulus (MPa) |
|---|---|---|---|---|
| I | 28 | 43 | Elvax ™ 240 | 9.0 |
| II | 28 | 25 | Elvax ™ 450 | 40.0 |
| III | 12 | 0.3 | Elvax ™ 670 | 77.0 |

TABLE 3

| Run No. | 26 | 27 | 28 |
|---|---|---|---|
| % PP | 95 | 80 | 90% |
| % Flexible Polymer | 5(EVA I) | 20(EVA II) | 10(EVA III) |
| Melt Temp. (°C.) | 226 | 224 | 229 |
| Chill Roll Temp. (°C.) | 57 | 57 | 57 |
| Chill Roll Contact Time(sec) | 0.73 | 0.73 | 0.73 |
| Caliper(microns) | 76 | 76 | 76 |
| Tensile Strength MD (kg/cm²) | 342 | 296 | 302 |
| Tensile Strength CD (kg/cm²) | 307 | 266 | 279 |
| Tear Strength MD (gm/ply) | 54 | 113 | 70 |
| Toughness CD aged (mm/sec) | 23 | 85 | 106 |

The data in Table 3 demonstrates that an ethylene/vinyl acetate flexible polymer can be substituted for the EDPM/PE flexible polymers to yield comparable films.

EXAMPLES 29-32

Film samples were prepared as in Examples 1-14, except that ethylene/acrylic acid copolymers having acrylic acid contents of 9% and 6.5% with melt indices of 1.5 and 9.0 respectively, available from the Dow

TABLE 4

| Run No. | 29 | 30 | 31 | 32 |
|---|---|---|---|---|
| % PP | 80 | 80 | 90 | 95 |
| % Flexible Polymer | 20(EAA I) | 20(EAA II) | 10(SIS) | 5 (SIS) |
| Melt Temp. (°C.) | 238 | 232 | 232 | 221 |
| Chill Roll Temp. (°C.) | 18 | 18 | 18 | 57 |
| Chill Roll Contact time (sec) | 0.37 | 0.37 | 0.37 | 0.73 |
| Caliper (microns) | 105 | 105 | 105 | 76 |
| Tensile Strength MD (kg/cm²) | 285 | 244 | 254 | 295 |
| Tensile Strength CD (kg/cm²) | 240 | 225 | 232 | 270 |
| Tear Strength MD (gm/ply) | 143 | 116 | 174 | 56 |
| Toughness CD (mm/sec) | 162 | 149 | 300 | 106 |

The data set forth in Table 4 demonstrates that ethylene/acrylic acid or styrene-isoprene-styrene flexible polymers can be substituted for the EDPM/PE flexible polymers to yield comparable films.

I claim:

1. A disposable diaper having attached thereto as a closure means a pressure-sensitive adhesive tape comprising:
   (a) a backing of a substantially untensilized, tough, ductile film, said film comprising a blend of crystalline isotactic polypropylene and a compatible polymer having a flexural modulus lower than that of said isotactic polypropylene, said film having
      (1) a longitudinal yield tensile strength of at least about 160 kg/cm²;
      (2) a transverse yield tensile strength of at least about 140 kg/cm²;
      (3) a longitudinal tear strength of at least about 50 gm/ply; and
      (4) a tensile impact toughness of greater than about 20 mm/sec; and
   (b) a coating of a pressure-sensitive adhesive on one side of said film.

2. A disposable diaper having attached thereto as a closure means a pressure-sensitive adhesive tape comprising:

(a) a backing of a substantially untensilized, tough, ductile film, said film comprising a blend of crystalline isotactic polypropylene and a compatible ethylene-propylene polymer having a flexural modulus lower than that of said isotactic polypropylene, said film having
   (1) a longitudinal yield tensile strength of at least about 160 kg/cm$^2$;
   (2) a transverse yield tensile strength of at least about 140 kg/cm$^2$;
   (3) a longitudinal tear strength of at least about 150 gm/ply; and
   (4) a tensile impact toughness of greater than about 120 mm/sec; and (b) a coating of a pressure-sensitive adhesive on one side of said film.

3. The disposable diaper of claim 2 wherein said film is comprised of about 65 to 99 weight percent crystalline isotactic polypropylene and about 35 to 1 weight percent of said compatible polymer.

4. The disposable diaper of claim 2 wherein said film is comprised of about 75 to 85 weight percent crystalline isotactic polypropylene and about 15 to 25 weight percent of said compatible polymer.

5. The disposable diaper of claim 2 wherein the pressure-sensitive adhesive comprises a rubber-resin adhesive.

* * * * *